United States Patent [19]

Wigness et al.

[11] Patent Number: 4,846,806
[45] Date of Patent: Jul. 11, 1989

[54] IMPLANTABLE INTRAVASCULAR ACCESS SYSTEM

[75] Inventors: Bruce D. Wigness; Frank D. Dorman, both of Minneapolis, Minn.

[73] Assignee: 501 Regents of University of Minnesota, Minneapolis, Minn.

[21] Appl. No.: 105,740

[22] Filed: Oct. 6, 1987

[51] Int. Cl.⁴ ............................................. A61M 31/00
[52] U.S. Cl. .................................... 604/175; 604/256; 604/891.1
[58] Field of Search ..................................... 604/27–30, 604/43, 96–99, 151, 153, 174, 175, 256, 278, 280, 283, 891.1

[56]  References Cited

U.S. PATENT DOCUMENTS

| | | |
|---|---|---|
| 3,331,371 | 7/1967 | Rocchi et al. . |
| 3,392,722 | 7/1968 | Jorgensen ............................ 604/256 |
| 4,240,433 | 12/1980 | Bordow . |
| 4,248,234 | 4/1981 | Assenza et al. . |
| 4,258,711 | 3/1981 | Tucker et al. ....................... 604/175 |
| 4,301,797 | 11/1981 | Pollack . |
| 4,505,710 | 3/1985 | Collins ................................ 604/891.1 |
| 4,536,179 | 8/1985 | Anderson et al. . |
| 4,657,536 | 4/1987 | Dorman . |
| 4,673,391 | 6/1987 | Kondo et al. ....................... 604/891.1 |
| 4,705,501 | 11/1987 | Wigness et al. . |
| 4,714,462 | 12/1987 | Di Domenico ..................... 604/891.1 |
| 4,718,893 | 1/1988 | Dorman et al. .................... 604/891.1 |

OTHER PUBLICATIONS

"Groshong® CV Catheter" brochure, 1986 Catheter Tech. Corp.

Primary Examiner—Stephen C. Pellegrino
Assistant Examiner—Ralph Lewis
Attorney, Agent, or Firm—Merchant, Gould, Smith, Edell, Welter & Schmidt

[57] ABSTRACT

An implantable intravascular access system, including an implantable, catheter obturator controller manifold for use with an implantable intravascular catheter. The catheter includes a lumen, having an expanded state and a normal state, an obturator, and an obturator plenum having an inflated state and a contracted state. The lumen can be closed or opened by hydraulically actuating the expansion or contraction of the obturator plenum when the lumen is in its normal state. When the obturator plenum is expanded to its inflated state, the obturator substantially blocks the lumen such that substantially no fluid can pass through the lumen when the lumen is in its normal state. The manifold comprises a housing, a receiving mechanism for receiving the catheter, an actuating mechanism for hydraulically actuating the expansion or contraction of the plenum, and a first entry mechanism for entering the housing.

26 Claims, 7 Drawing Sheets

U.S. Patent   Jul. 11, 1989   Sheet 1 of 7   4,846,806

IMPLANTABLE INTRAVASCULAR ACCESS SYSTEM

FIELD OF THE INVENTION

The present invention relates to an implantable intravascular access system, specifically an implantable, catheter obturator controller manifold for intravascular catheters with hydraulically operated self-contained obturators. It is designed to provide long term vascular access for chronic drug infusion, blood sampling, or the like. It is also designed to prevent blockage by blood clotting or thrombosis during long periods of time when the device is out of use. This application is related to co-pending U.S. patent application Ser. No. 367,683 now U.S. Pat. No. 4,705,501 entitled "Bi-Directional, Anti-Reflux Vascular Access System".

BACKGROUND OF THE INVENTION

It is not uncommon for patients undergoing therapeutic medical treatment to receive frequent vascular injections or infusions of therapeutic fluids. Other medical treatments require frequent withdrawal or infusion of blood. There are many other medical circumstances which require chronic vascular access. They include therapeutic requirements for the following: neonatal umbilical vein cannulation, hyperalimentation, chemotherapy, permanent intravascular site for portable drug infusion devices, other drug therapy such as osteomylitis and fungal infections, blood pressure monitoring, hemodialysis, plasmapherisis, and repeated blood sampling.

In the past, such chronic infusions or blood withdrawals required repeated punctures through the skin. Today, most of these procedures are performed using percutaneously placed or cannulated intravascular catheters. Examples include the implantable catheter disclosed by Anderson et al. (U.S. Pat. No. 4,536,179) which discloses a catheter for long term implantation. This catheter is made of a flexible, inert, nontoxic and biocompatible polymeric material having a thin flurocarbon coating, achieved by glow discharge plasma polymerization on at least one of the contacting surfaces which prevents self-adhesion of the cured polymer surfaces.

Examples of other catheters include central venous catheters generically termed subclavian catheters. Intravascular access catheters in this category are generally made of plastic or rubber tubes with female luer fittings at one end. Catheters of this type are usually selected for short-term therapy. In order to extend the useful life if this type of catheter, the catheter lumen is often filled with a solution containing an anticoagulant between uses (e.g., heparin). This is necessary in order to prevent blood from coagulating in the catheter lumen, thereby occluding the catheter and preventing its further use. Since the anticoagulant constantly diffuses from the lumen into the blood stream, however the catheter must be refilled with the anticoagulant solution every 2-3 days in order to prevent a clot from forming in the catheter tip.

This problem has been circumvented to a certain degree by the Shiley Vas-Cath Catheter (Shiley, Inc., Irvine, CA) which is a transcutaneous subclavian catheter which differs from the prior art subclavian catheters in that it is essentially two coaxial tubes with the inner tube being removable. Each time a catheter clots off, the inner tube, which contains the clot, is extracted from the outer tube and replaced with a fresh inner tube.

Another solution to the problem of clotting in the catheter lumen, involves the insertion of a solid flexible plastic rod or obturator into the catheter lumen between uses. The obturator completely occupies the catheter lumen, thereby preventing the diffusion of blood into the lumen where it might subsequently form a clot.

Medical procedures requiring long-term vascular access, however, require totally implantable products in order to limit the risk of infection. Several implantable devices have been designed which provide a metal or plastic housing containing a rubber septum which is specially constructed to undergo repeated punctures. Unfortunately, there catheters have no features to prevent clotting by blood components other than their small lumen diameters which provide some limitation on the diffusion of blood into the lumen. Although these catheters are generally filled with a solution containing an anticoagulant between uses, if the time interval between catheter uses is relatively long (e.g. weeks instead of days), each therapy session must be initiated by blowing the clotted material into the vasculature. Obviously, this is not particularly desirable as the blood clot may initiate further clotting and could possibly result in an embolism or other serious vascular disorder.

Unfortunately, Shiley Vas-Cath Catheter discussed above and other designs featuring solid removable obturators, are not suited for total implantation. This is because such a modification would require a relatively large solid element to be passed through the skin, subcutaneous tissure, and catheter septum with each use.

Diffusion or aspiration of blood into the catheter may be prevented by adding a check valve to the intravascular tip of the catheter. Such a check valve is disclosed in Dorman U.S. Pat. No. 4,657,536) which describes a sleeve-type one-way check valve design for this purpose. While this design prevents blood components from clotting the tip, it allows only infusion of liquids and does not allow withdrawal of blood samples which is often desirable maneuver to be carried out with intravascular access catheters.

A two-way check valve located at the tip of the catheter is less susceptible to clotting and allows for infusion of fluids as well as the withdrawal of blood samples. One commercially available percutaneous catheter which has a two-way check valve is the Groshong Catheter (Catheter Technology Corp., Salt Lake City, UT). This catheter features a slit valve at the tip of the catheter which allows both aspiration of blood and infusion of fluids and yet precludes the diffusion of blood components into the lumen between therapy sessions. Although this catheter is currently a percutaneous appliance, it would be conceivable to make such a catheter into an implantable device by replacing the female luer fitting with an implantable septum. The major drawback to slit valve check valves, however, is unreliability, which bodes poorly for long term use. Their "valving" performance depends upon the elastic forces within the catheter wall. These forces must be strong enough to return the valve to the relaxed or closed position between uses. Construction of the device with a tight fitting closed state results in a stiff catheter in which reliability is achieved at the expense of mechanical flexibility and bio-incompatibility with respect to interaction between the catheter and the endothelial lining of the vessel being cannulated.

It will be appreciated from the foregoing that prior art devices present problems which are in need of solutions. The present invention provides solutions for these and other problems.

SUMMARY OF THE INVENTION

The present invention is directed to an implantable, catheter obturator controller manifold for use with an implantable intravascular catheter including a lumen having a normal state and an expanded state, an obturator, and an obturator plenum having an inflated state and a contracted state. The lumen can be opened or closed when it is in its normal state by hydraulically actuating the expansion or contraction of the obturator plenum. When the obturator plenum is expanded to its inflated state, the lumen is substantially blocked by the obturator when the lumen is in its normal state such that substantially no fluid can pass through the lumen. The catheter obturator controller manifold comprises: a housing; first entry means for entering the housing; receiving means for receiving the catheter in the housing and actuating means for hydraulically actuating the contraction or expansion of the obturator plenum. The actuating means include a manifold chamber within the housing which is in fluid communication with the catheter, and an amount of a hydraulic fluid effective to actuate the expansion and contraction of the obturator plenum. The fluid is contained in the hydraulic fluid subchamber and the obturator plenum. The amount or fluid is sufficient to allow the obturator to effectively block the lumen when the lumen is in its normal state and the obturator plenum is expanded to its inflated state. The manifold chamber includes at least two subchambers which are separated from each other, a fluid pathway subchamber which is in fluid communication with the lumen of the catheter and the first entry means, and a hydraulic fluid subchamber which is in fluid communication with the obturator plenum. The fluid pathway subchamber and the hydraulic fluid subchamber are expandable and contractible.

Preferably, the first entry means include a puncturable, self-sealing, resilient access septum which seals the first entry means. Fluids, such as medications or blood, may be infused into or withdrawn from the catheter lumen when the lumen is open by means of a hypodermic needle inserted through the access septum. The manifold preferably includes adjusting means for adjusting the amount of hydraulic fluid within the hydraulic fluid subchamber and the obturator plenum. The adjusting means preferably include second entry means for entering the housing. The second entry means are in fluid communication with the hydraulic fluid subchamber and include puncturable, self-sealing, resilient priming septum which seals the second entry means. The amount of hydraulic fluid in the hydraulic fluid subchamber may be adjusted by infusing fluid into, or withdrawing fluid from, the hydraulic fluid the priming septum.

The present invention also provides an implantable, intravascular access system comprising the implantable, catheter obturator controller manifold disclosed herein and a flexible intravascular catheter also disclosed herein. These embodiments of the present invention share many of the advantages offered by other vascular access devices wherein the lumen may be closed when it is not in use. These advantages include resistance to occlusion from thrombosis, decreased risk of air embolism, and lowered maintenance requirements (e.g., heparinization and irrigation). Because the obturator controller manifold and the vascular access system of the present invention are also totally implantable, they offer the following additional advantages: longer useful life due to reduced risk of infection; fewer recannulations and, therefore, less discomfort to the patient; and more patient freedom because the device allows the patient to shower, bathe, or swim without having to perform any special catheter maintenance.

The co-pending Wigness et al. patent application (U.S. Ser. No. 367,683 now U.S. Pat. No. 4,705,501) claims a totally implantable, intravascular access device featuring means for closing the catheter 1 when not in use. The operation of that device, how as described in the original disclosure, requires to both the obturator plenum and the catheter by puncturing different rubber septums. It is to perform both operations serially with a s skin puncture if the septums are stacked. This one to puncture the first septum and enter the directly beneath it; perform the obturator shift step; advance the needle, puncture the second septum and enter the bottom chamber; perform the drug infusion or blood aspiration; withdraw the needle from the bottom chamber and stop when the tip of the needle is in the top chamber; shift the obturator to the closed lumen state; and withdraw the needle from the body.

Because this sequence of steps is difficult to properly carry out, it is more likely that the two septums would be arranged side by side, meaning that two separate skin punctures would be necessary. Therefore, the invention disclosed in the co-pending Wigness et al. application would either require two separate skin punctures, thereby causing additional patient discomfort and lower patient acceptance compared to catheters requiring a single skin puncture, or a sequence of steps which are difficult to properly carry out.

The embodiments of the present application make it possible to subject a patient to a single skin puncture per procedure. Once the skin is punctured and a hypodermic needle is inserted in the manifold of the present invention, the needle can be used to manipulate elements of the manifold and to thereby hydraulically actuate the opening and closing of the catheter lumen. This may require changing the body of the syringe connected to the hypodermic needle once it is inserted through the skin and into the manifold, or a multiple stop-cock arrangement on the syringe such that different fluids may be infused or withdrawn through the needle, thereby utilizing separate chambers and/or connection ports. In certain embodiments, the catheter lumen is opened by using the hypodermic needle to depress a rigid bellows diaphragm connected to a bellows, or a piston connected to telescoping means, which cooperate to expand the hydraulic fluid subchamber, thereby withdrawing fluid from the obturator plenum, contracting the plenum, and opening the catheter lumen. When the catheter lumen is in its normal state, it is closed by withdrawing the needle thereby allowing the diaphragm or piston to return to its normal position, thereby expanding the obturator plenum to its inflated state and closing the catheter lumen.

In another embodiment, the hypodermic needle is used to abruptly withdraw or aspirate fluid from the fluid pathway subchamber, thereby shifting a separation diaphragm away from a stable position, preferably a first stable position, preferably to a second stable position, thereby expanding the volume of the hydraulic fluid subchamber. When the volume of the hydraulic fluid subchamber expands, fluid s withdrawn from the obturator plenum, thereby contracting the obturator plenum and opening the catheter lumen. The change in volume of the hydraulic fluid subchamber is substantially equal to the change in volume of the obturator plenum. Once the catheter lumen is open, he hypodermic needle may be connected with a syringe device for infusing fluid into, or withdrawing or aspirating fluid from, the intravascular system of the body as desired. Following this procedure, the needle may be connected to another syringe to infuse a neutral solution such as a saline solution or the like, in order to irrigate the fluid pathway subchamber and the catheter lumen prior to closing the catheter lumen. Fluid is subsequently infused into the fluid pathway subchamber with enough pressure to shift the separation diaphragm to its stable position or first stable position, thereby expanding the obturator plenum to its inflated state and closing the catheter lumen when the lumen is in its normal state. The needle can then be withdrawn.

In preferred embodiments, fluid may be infused through the catheter lumen into the body when the obturator plenum is in its inflated state by infusing fluid into the fluid pathway subchamber with sufficient force to expand an outer wall of the catheter such that the catheter lumen is in its expanded state, thereby allowing fluid to pass through the lumen. In such a case, the lumen is open to the passage of fluid through the lumen only as long as sufficient fluid pressure is present to expand the catheter so that the lumen is in its expanded state. When the fluid pressure is no longer sufficient to expand the flexible catheter, the lumen returns to its normal state and the lumen is closed.

In summary, it will be appreciated that it is desirable to have an implantable vascular access system in which the catheter lumen may be closed when it is not in use, because such a catheter would be resistant to occlusion from thrombosis. Furthermore, such a catheter requires less maintenance.

It will be further appreciated that such a vascular access system, which is totally implantable, offers a longer useful life due to the reduced risk of infection. In addition, it requires fewer recannulations and, therefore, less discomfort to the patient. Furthermore, patients using this device have more freedom because they are free to take a shower, to bathe, or to swim without having to perform any special catheter maintenance in response to such activity.

The above described features and advantages along with various other advantages and features of novelty are pointed out with particularity in the claims of the present application. However, for a better understanding of the invention, its advantages, and objects attained by its use, reference should be made to the drawings which form a further part of the present application and to the accompanying descriptive matter in which there is illustrated and described preferred embodiments of the invention.

DETAILED DESCRIPTION OF EMBODIMENTS OF THE INVENTION

Figure 2:
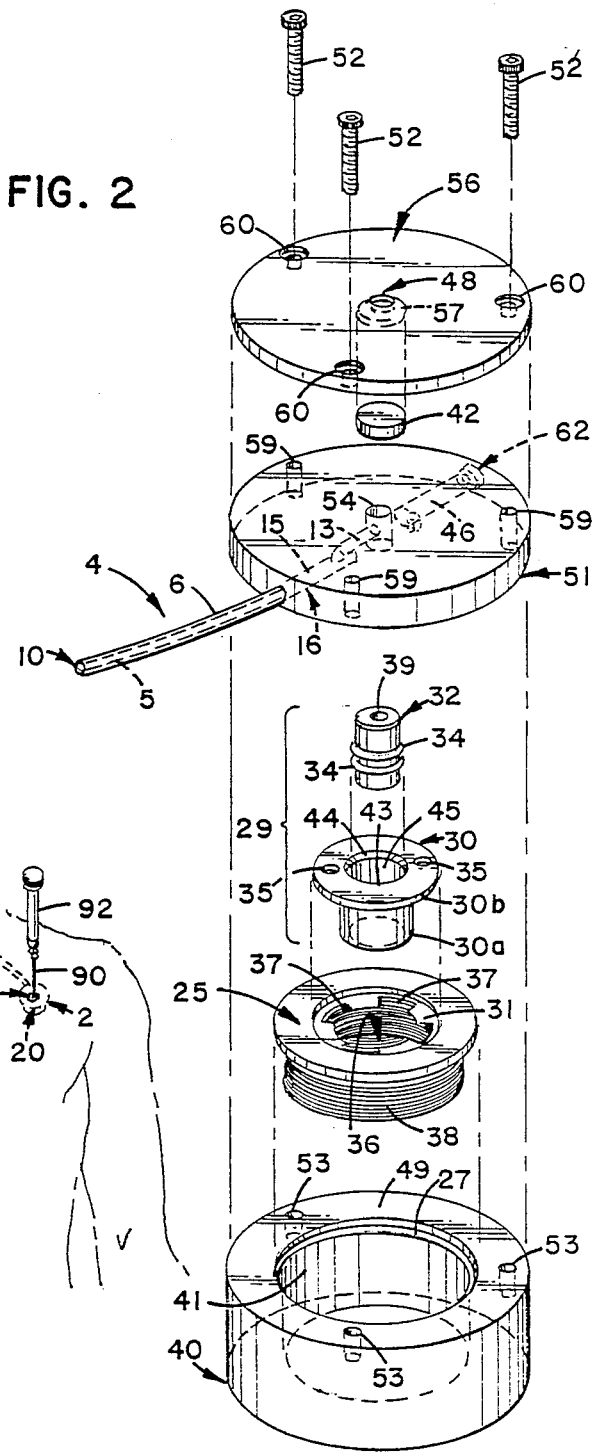
FIG. 2 is an exploded, perspective view of an embodiment of an intravascular access system in accordance with the principles of the present invention having a telescoping mechanism for expanding the fluid pathway subchamber and a bellows mechanism for expanding the hydraulic fluid subchamber.
Figure 1:
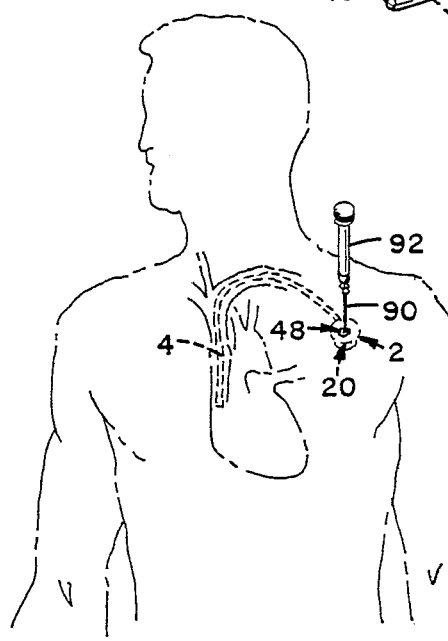
FIG. 1 is an elevated, perspective view of an embodiment of an implantable intravascular access system including a catheter obturator controller manifold and a catheter, implanted under the skin of a patient, with a hypodermic needle being inserted into the controller manifold.

Referring to th drawings, FIG. 1 shows an embodiment of an implantable, intravascular access system in accordance with principles of the present invention, the intravascular access system being referenced generally by the reference numeral 2. The intravascular access system 2 includes an implantable catheter obturator controller manifold, being generally referenced by the reference numeral 20, and an implantable intravascular catheter 4. The intravascular access system 2 is drawn in phantom under the skin of a patient. A hypodermic needle 90, connected to a syringe 92, is shown in phantom passing through the patient's skin and into the manifold 20 through the first entry mechanism 48. FIG. 2 shows an exploded, perspective view of a prototype of the intravascular access system 2 shown in FIG. 1. Preferably, the elements of the manifold 20 are either bonded or welded together and do not have screws or bolts in preferred embodiments. This is because elements which are fused together are better sealed, and sealed in a manner which is generally considered to be more compatible with an implantable device. Enlarged cross-sectional schematic views of a preferred embodiment wherein the elements are bonded together are presented in FIGS. 3-8.

The present invention includes an implantable catheter obturator controller manifold 20 designed to control the opening and closing of an implantable intravascular catheter 4. Referring now to the embodiment shown in FIGS. 3 and 4, the manifold 20 comprises a housing 18, a first entry mechanism 48 for entering the housing 18, a receiving mechanism 16 for receiving the catheter 4 in the housing 18, and an actuating mechanism, generally referenced by the reference numeral 22, for hydraulically actuating the contraction or expansion of an obturator plenum 11 of the catheter 4.

Figure 3:
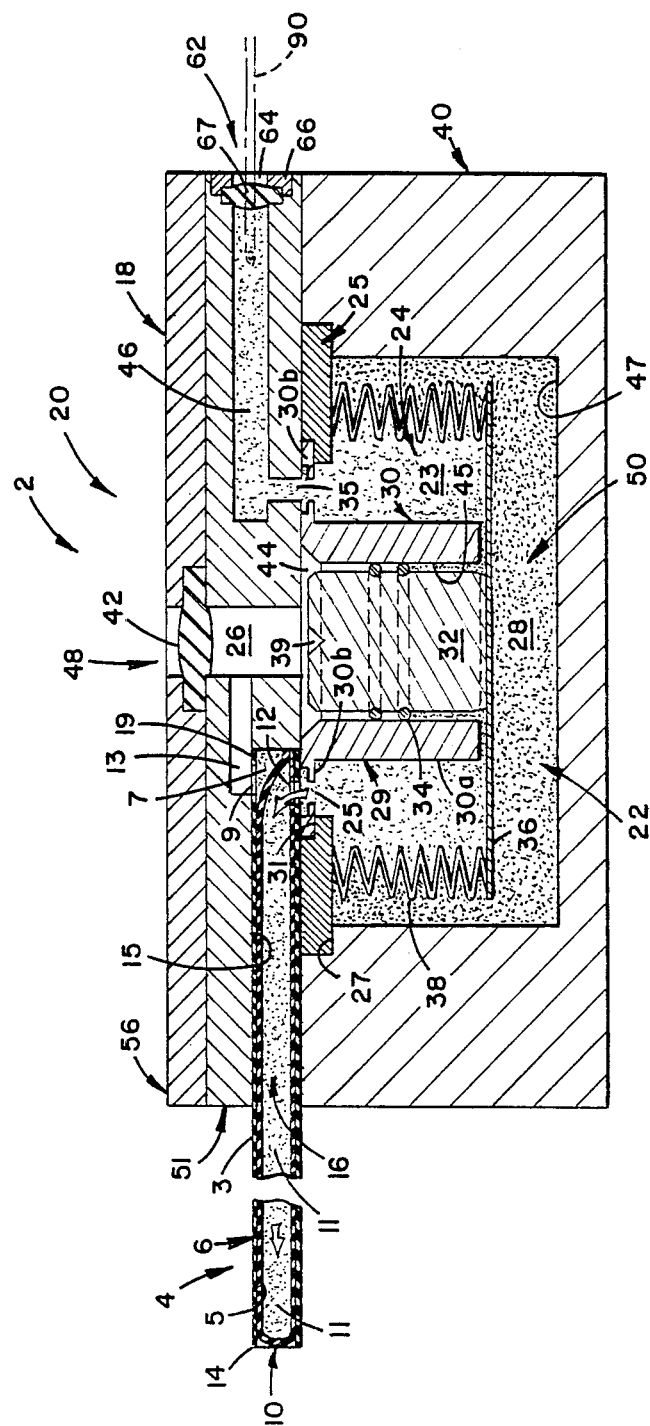
FIG. 3 is an enlarged cross-sectional schematic view of the embodiment shown in FIG. 2 taken generally through the center of the catheter and catheter obturator manifold when the hydraulic fluid subchamber is contracted such that the obturator plenum is fully expanded and the catheter lumen is closed.

The catheter is preferably made of a flexible, biocompatible, rubber or synthetic rubberlike material, preferably silicone rubber. This material is preferably expandable under increased fluid pressure, and will contract to a normal state when the pressure returns to normal In the embodiment shown in FIGS. 3 and 4, the implantable catheter 4 includes inner and outer flexible tubes, 10 and 6 respectively, of substantially the same length and substantially concentric shape. The inner tube 10, also referred to herein as an obturator 10 is a collapsable tube which is closed at a distal end 14 of the catheter 4. The outer tube 6 forms an outer wall 5 of the catheter 4, which cooperates with the obturator 10 to define a catheter lumen 7. Inside the obturator 10 is a space 11, also referred to herein as an obturator plenum 11, which is defined by the obturator 10 and filled with hydraulic fluid which can pass through an obturator opening 12 in the obturator 10 and the outer tube 6 proximate the proximal end 19 of the catheter 4. The obturator opening 12 provides fluid communication between the obturator plenum 11 and a hydraulic fluid subchamber 24 of the manifold 20. The catheter wall 5 is preferably joined to the obturator 10 in the area surrounding the obturato opening 12. In FIG. 3, the obturator plenum 11 is expanded such that the plenum 11 is in an inflated state, thereby closing the lumen 7, which is in a normal state, such that the obturator 10 substantially blocks the catheter lumen 7 so that substantially no fluid can pass through the lumen 7 when it is in the normal state In FIG. 4, fluid has been withdrawn from the obturator plenum 11 such that the plenum 11 contracts and the obturator 10 no longer blocks the catheter lumen 7 which is open, thereby allowing fluids to pass through the lumen 7. In this figure the plenum 11 is in a state.

The manifold 20 is designed receive the obturator catheter 4 and to actuate expansion and contraction of the obturator plenum 11, thereby opening and closing the catheter lumen 7 when the lumen 7 is in its normal state to allow long-term intravascular access, while largely preventing the of thrombosis which might otherwise block the lumen 7 and prevent its use. In order to or manipulate the expansion or contraction of the obturator plenum 11, embodiments of the present invention designed to include the housing 18 having a mechanism 16 including a catheter receiving pas 15 for receiving the proximal end 19 of the 4, such that the obturator plenum 11 is in fluid communication with the actuating mechanism 22 for hydraulically actuating the contraction or expansion the obturator plenum 11. The actuating mechanism 22 a manifold chamber 50 within the housing 18. The manifold chamber includes three subchambers which are separated from each other, the hydraulic fluid s 24 in fluid communication with the obturator 11 via the obturator opening 12, a fluid pathway s 26 in fluid communication with the lumen 7 catheter 4 as well as with the first entry mechanism 48, and an expansion subchamber 28. The hydraulic subchamber 24 and the obturator plenum 11 contain an amount of a hydraulic fluid effective to actuate expansion and contraction of the obturator plenum such that the obturator 10 effectively blocks the lumen 7 when the obturator plenum 11 is expanded to its inflated state and the lumen is in its normal state. The actuating mechanism 22 of this embodiment of the present invention includes a bellows 38, which is attach to the housing 18 and a bellows diaphragm 36. These e cooperate to separate the fluid pathway 24 from the expansion subchamber 28. The hydraulic subchamber 24 is separated from the fluid pathway 26 by a telescoping mechanism 29. Preferably 38 and the telescoping mechanism 29 arranged concentrically. The telescoping 29 includes a collared sleeve 30 which is des be slightly larger than a piston 32 which is inserted inside of a sleeve portion 30a of the collared 30. The piston 32 is equipped with two resilient O-rings 34, such that the piston 32 is slideably e within the sleeve portion 30a, thereby providing seal such that there is substantially no fluid communication between the fluid pathway subchamber 26 and th fluid subchamber 24.

Figure 4:
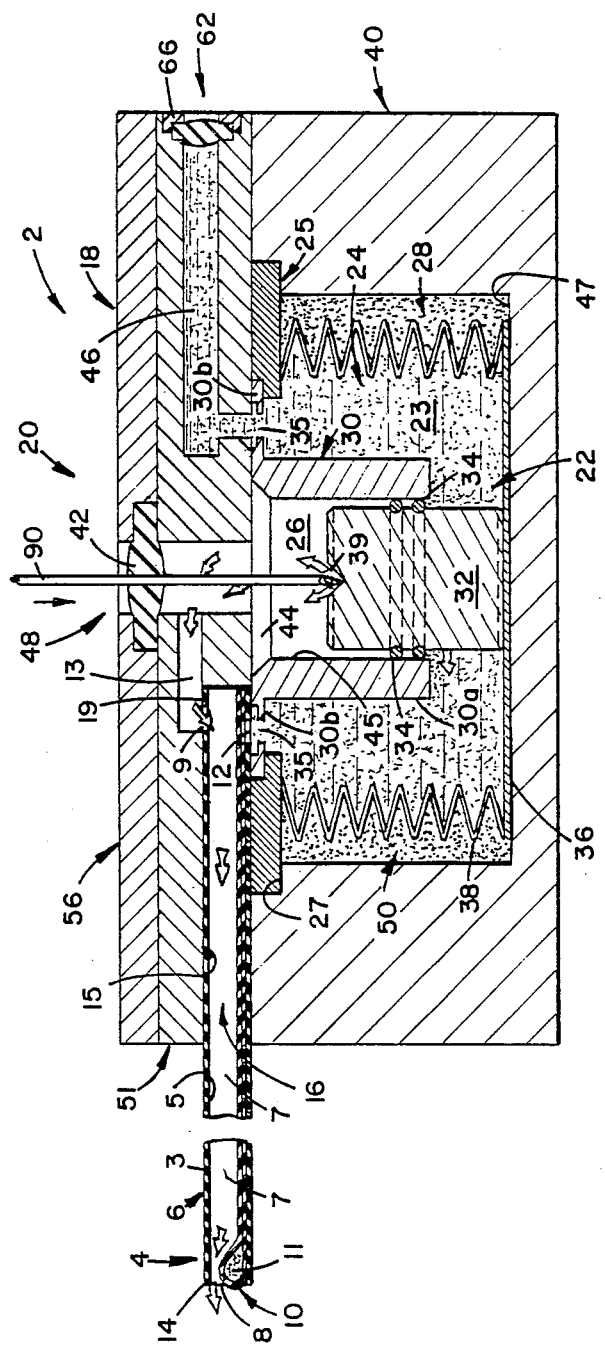
FIG. 4 is a view similar to that of FIG. 3 illustrating the embodiment shown in FIG. 2 when the fluid pathway subchamber and the hydraulic fluid subchamber are expanded such that the obturator plenum is contracted and the catheter lumen is open.

The obturator plenum 11 may be contracted in order to open the catheter lumen 7 b depressing the piston 32 with an hypodermic needle 90. The normal, or dormant position of this embodiment, the intravascular access system 2 is not in active use, is shown in FIG. 3. The expansion subchamber contains a compressible gas, preferably a fluorocarbon or the like, having a boiling point below the normal human body temperature of 37° C., e.g., about 20°-35° C. The amount of gas in the expansion subchamber 28 is such that the volume of hydraulic fluid in subchamber 24 reaches an equilibrium with the volume occupied compressible gas in the expansion subchamber 28 when the hydraulic fluid subchamber 24 is contracted such that the obturator plenum 11 is expanded to its inflated state and the catheter lumen 7 is closed when it in its normal state. These relationships are shown FIG. 3. In order to open the catheter lumen 7, a hypodermic needle 90 may be inserted through the access septum 42 to depress the piston 32, thereby depressing the bellows diaphragm 36. The piston 32 has a depression 39 for receiving the hypodermic needle 90. As the needle 90 depresses the piston 32 and the diaphragm 36, the hydraulic fluid subchamber 24 and the fluid pathway subchamber 26 expand in substantial relation to the contraction of the expansion subchamber 28. When the diaphragm 36 is depressed to a bottom surface 47 of the expansion subchamber 28, as shown in FIG. 4, the hydraulic fluid subchamber 24 has bee expanded such that fluid has been withdrawn from the obturator plenum 11, thereby contracting the obturator plenum 11 and the obturator 10 such that the catheter lumen 7 is open. In this position fluid may be infused into the hydraulic fluid subchamber 26 and may then flow a catheter access opening 9 in the proximal end 19 of the catheter 4, into the catheter lumen 7 and out the catheter lumen 7 through the catheter opening 8. Body fluids, preferably blood, can be withdrawn or aspirated from the body through the catheter lumen 7 when this embodiment is in this position. Fluid is withdrawn from the fluid pathway subchamber 26 until the body fluids are drawn into the catheter lumen 7, into the fluid pathway subchamber 26, and into the hypodermic needle 90 and out of the mainfold 20.

In another embodiment, the 4 has sufficient elasticity to allow fluids to be infused into the body through the manifold 20 without depressing the diaphragm 36 in order to open the lumen 7, because the flexibility of the catheter 4 allows fluids, which are infused into the fluid pathway subchamber 26 under sufficient fluid pressure to expand the cath lumen 7 to its expanded state, to pass through the catheter lumen 7 and into the body despite the fact that the obturator plenum 11 is in its inflated state which would otherwise be sufficient to close the lumen 7. In this embodiment therefore, the diaphragm 36 need not depressed to open the lumen 7 in order to allow fluid to be infused into the body.

Figure 8:
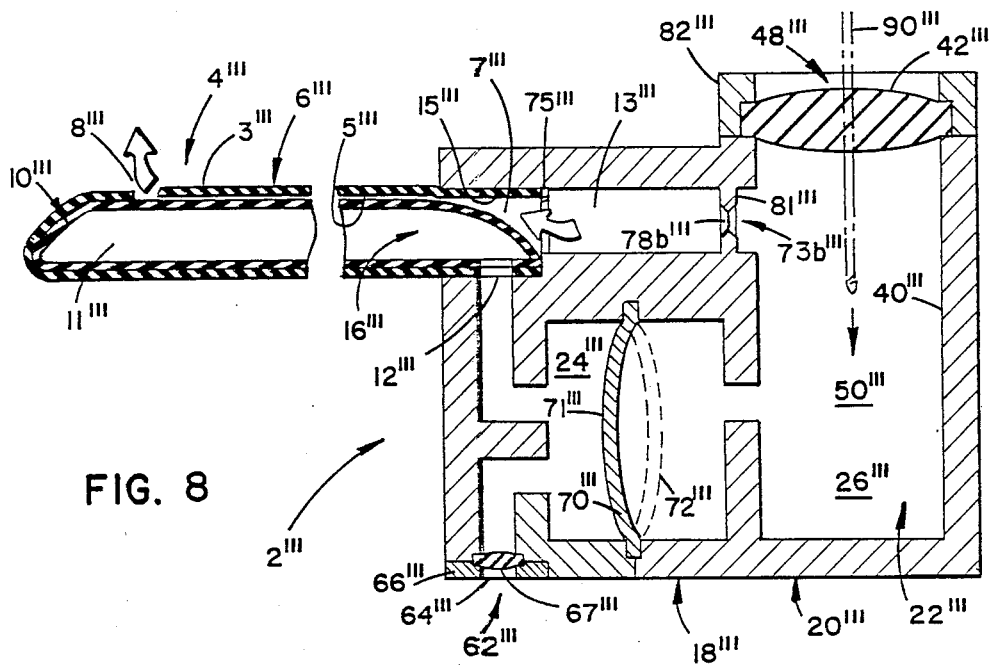
FIG. 8 is an enlarged cross-sectional schematic view similar to FIG. 7A of an intravascular access system including a monostable separating diaphragm.

When the fluid pathway subchamber 26 is filled with body fluids which have passed through the catheter opening 8 into the lumen 7, through the catheter access opening 9 and into the fluid pathway subchamber 26, the syringe connected to the hypodermic needle 90 may be changed, or a stop-cock system may be used to change an access line to the hypodermic needle 90, such that the body fluids in the fluid pathway subchamber 26 may be withdrawn using a new reception chamber to receive the body fluids. When a suitable sample has been withdrawn, the connection to the hypodermic needle 90 may be changed again, and the fluid pathway subchamber 26 and the catheter lumen 7 may be irrigated with a suitable solution, such as a saline solution or an antiseptic solution, in order to wash the body fluids out of these areas. When the infusing and/or sampling procedures have been completed, the hypodermic needle 90 may be withdrawn such that the hydraulic fluid subchamber 24 contracts, thereby forcing hydraulic fluid into the obturator plenum 11. This expands the obturator plenum 11 to its inflated state so that obturator 10 substantially blocks the catheter lumen 7, when the lumen 7 is in its normal state, such that the lumen 7 is closed and substantially no fluids may pass through the lumen 7. The contraction of the hydraulic fluid subchamber 24 when the hypodermic needle 90 is removed is preferably driven by the compressed gas in the expansion subchamber 28. In alternate embodiments, a resilient mechanism, such as a spring or a coil spring, the spring force of a bellows mechanism, a resilient air bag, or the like, could be used to return the diaphragm 36 to the normal, or dormant position. While it is always necessary to contract or collapse the obturator 10 and open the lumen 7 in order to aspirate or withdraw fluids from the body, or to perform the aspiration function, it is possible to infuse fluids into the body when the obturator plenum 11 is in the inflated state. This is because of the elasticity of the tube outer 6 of the catheter 4 which expands so that the plenum 11 is in its expanded state when the fluids are infused under sufficient fluid pressure to expand the plenum 11 to this state. Fluids infused into the fluid pathway subchamber 26, are then allowed to pass through lumen 7 when delivered under sufficient fluid pressures. In FIG. 8 the catheter lumen 7''' of an alternate embodiment is shown in such an expanded state, while the obturator plenum 11''' is in an inflated state, allowing fluids to pass through the lumen 7''' and into the body.

FIG. 2 is an exploded perspective view of a prototype of the embodiment shown FIGS. 3 and 4. At the bottom of FIG. 2, the manifold 40 is shown having a hollow portion 41 designed to accomodate the bellows 38 and the diaphragm 36. The bellows 38 are attached to a hydraulic fluid manifold washer 25 which sits on a manifold body ledge 27 when the washer 25 and bellows 38 are assembled and in place with the manifold body 40. The hydraulic fluid manifold washer 25 has a ledge 31 for receiving a collared sleeve member 30 having a sleeve portion 30a and a collar portion 30b. The collar portion 30b has two openings 35 which must be aligned with one of four recesses 37 in the manifold washer ledge 31. These openings allow fluid communication between the hydraulic fluid subchamber 24 and the obturator plenum 11, and between the main portion 23 of the hydraulic fluid subchamber 24 and the priming passageway 46. Once the washer 25 and the collar portion 30b are aligned and assembled in place, the piston 32 having two resilient O-rings 34 around its cylindrical circumference may be inserted through the piston opening 43 in the collar portion 30b and into the sleeve portion 30a. The sleeve member 30 bevelled edge 44 which surrounds the opening 43 so as to facilitate insertion of the sleeve member 30. The upper portion 51 of the manifold 50 may then be placed upon the upper surface 49 of the manifold body 40. It must be aligned so that screws 52 may be inserted through the upper portion screw holes 59 and into manifold body screw holes 53. The priming passageway 46 and the catheter reception pathway 15 must also be aligned with the openings 35 in the sleeve washer 33 in order for fluid in the main portion 23 of the hydraulic fluid subchamber 24 can communicate with the priming passageway 46 and the obturator plenum 11 through these openings. The upper portion 57 of the manifold 50 also includes a catheter access passageway 13 which, along with the priming passageway 46, and the catheter receiving passageway 15 are shown in phantom in FIG. 2. The catheter access passageway 13 is a portion or a section of the fluid pathway subchamber 26. Also shown partially in phantom is a cylindrical opening 54 in the upper portion 51 of the manifold 50 which will comprise another portion of the fluid pathway subchamber 26 and which communicates with the catheter receiving passageway 15 through the catheter access passageway 13. The final steps in assembling the manifold shown in FIG. 2 include placing the access septum 42 on top of the cylindrical opening 54, placing the manifold cap 56 on top of the upper portion 51 such that a septum opening 57 for receiving the access septum 42 (shown in phantom in FIG. 2) receives the access septum 42 and the screw holes 60 are properly aligned so that the screws 52 may be inserted in the appropriate parts of the manifold 20, inserting the screws 52 and tightening them down thereby completing the assembly of the manifold. In the process of tightening down the screws 52, the access septum 42 will be squeezed into a space which is slightly smaller than the septum around the edges of the septum, thereby allowing for a tight seal. The second entry means 62 includes a smaller priming septum 67 at the distal end of the priming passageway 46. It is pressed into place by a circular washer 66 which is sealingly engaged to the upper portion 51 of the manifold 50. The washer 66 is sealed to the upper portion 51 using biocompatible sealant, preferably a silicone rubber sealant such as Silastic TM Medical adhesive silicone type A sealant from Dow-Corning, Inc. It should be understood that the device shown in FIG. 2 is a prototype, and that it is preferable to seal the joints between elements of the manifold in a manner which fuses the elements together, such as a process of bonding or welding, rather than bolting or screwing the device together. Preferably, the device shown in FIG. 2 is made of a biocompatible plastic and includes the use of a biocompatible sealant to seal all joints of and in spite of and in addition to the use of screws to construct the manifold.

Figure 5:
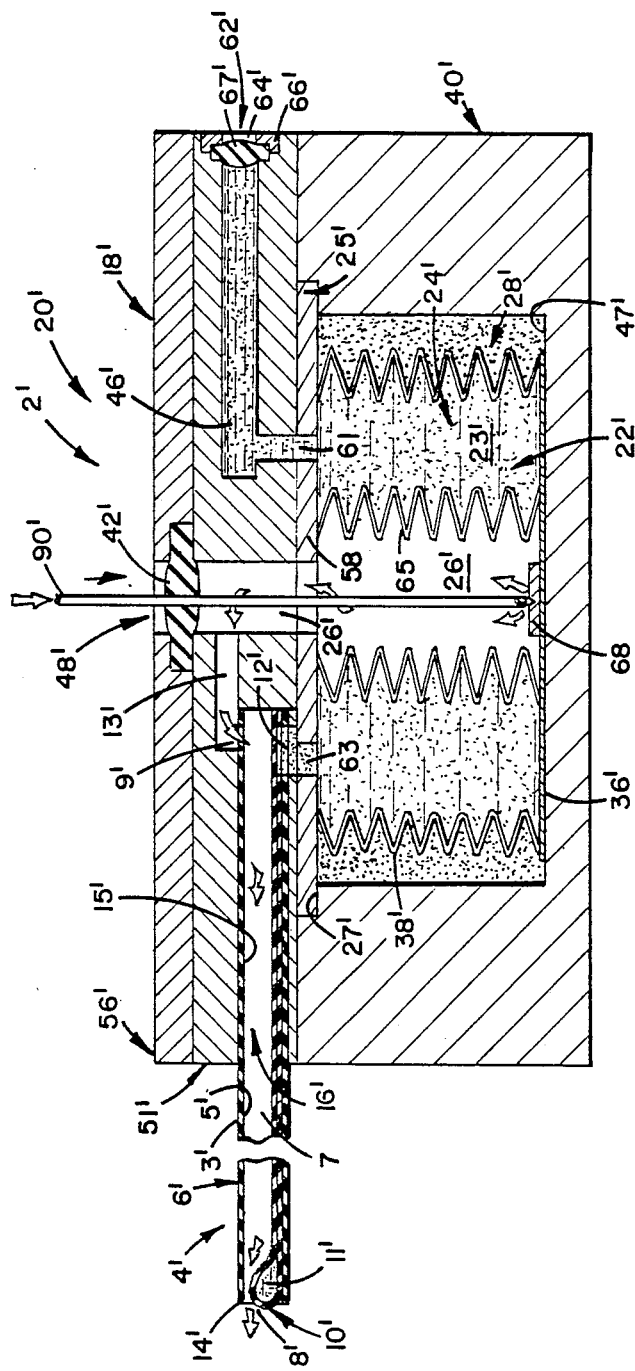
FIG. 5 is a view similar to that of FIG. 3 of an alternate embodiment of an intravascular access system having bellows mechanisms separating the fluid pathway subchamber from the hydraulic fluid subchamber and the hydraulic fluid subchamber from the expansion subchamber, wherein the hydraulic fluid subchamber and the fluid pathway subchamber are expanded such that fluid has been withdrawn from the obturator plenum and the catheter lumen is open.
Figure 6:
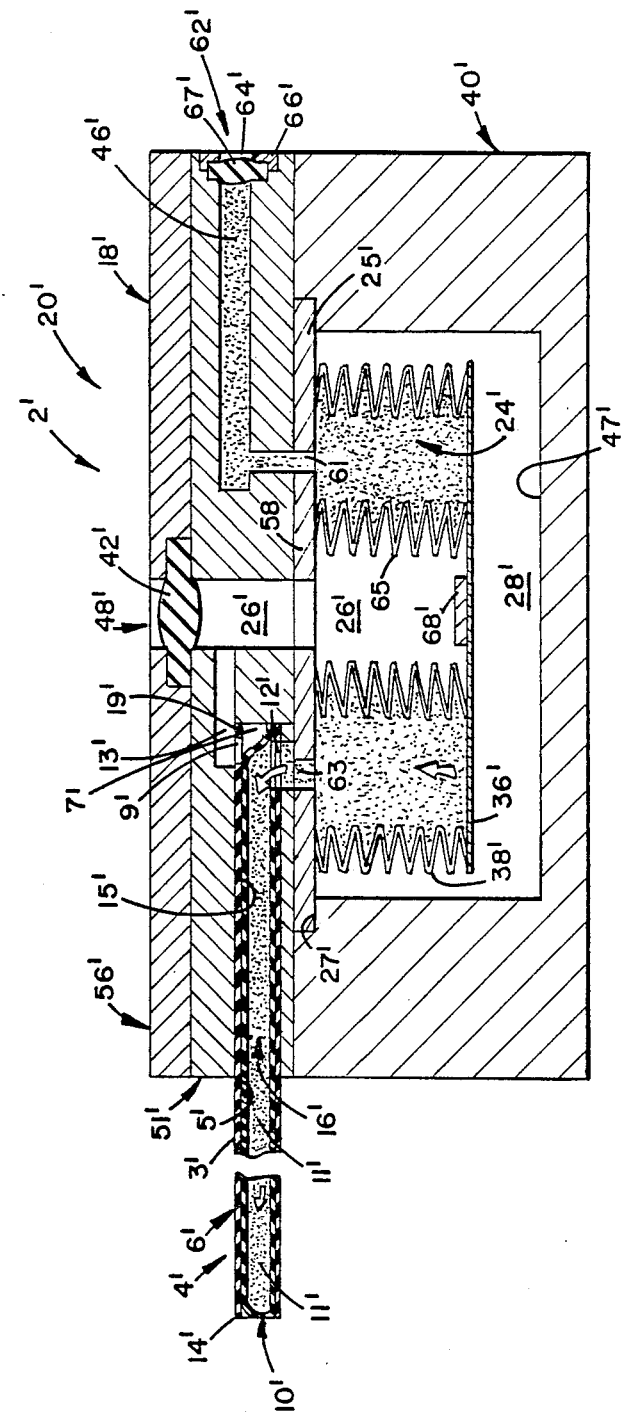
FIG. 6 is a view similar to that of FIG. 3 of the embodiment shown in FIG. 5, wherein the hydraulic fluid subchamber and the fluid pathway subchamber are contracted such that fluid has fully expanded the obturator plenum and the catheter lumen is closed.

FIGS. 5 and 6 show schematic representations of an alternate embodiment of the present invention (elements corresponding to elements shown in FIGS. 1, 2, 3, and 4, are designated by primed reference numerals), wherein the hydraulic actuating mean 22' includes two concentric bellows 38' and 65 attached to the housing 18' and the rigid bellows diaphragm 36'. The first or outer of the two concentric bellows 38' separates the hydraulic fluid subchamber 24' from the expansion subchamber 28'. The second or inner of the two concentric bellows 65 functions in place of the telescoping mechanism 29 shown in FIGS. 3 and 4. This bellows 65 separates the fluid pathway subchamber 26' from the hydraulic fluid subchamber 24'. The diaphragm 36' is equipped with a resilient needle stop 68 which is designed to receive the tip of a hypodermic needle, as is shown in FIG. 5. This embodiment of the present invention has many of the same features as the embodiment shown in FIGS. 3 and 4. It also operates in a very similar manner. The primary differences is the use of an inner bellows 65 to function in the place of the telescoping mechanism 29. Other differences include replacement of the collar portion 30b a manifold washer 25 with single dual bellows washer 58 which sits on the manifold body ledge 27'. Both be 38' and 65 are attached to the bellows washer 58 and to the diaphram 36' such that there is substantially no fluid communication between and of the subchambers. The bellows washer 58 contains a priming opening 61 and a catheter receiving opening 63 The passageway opening 61 allows fluid communication the primary passageway 46' and the main 23' of the hydraulic fluid subchamber 24'. The receiving opening 63 cooperates with the 12' to allow fluid communication between fluid subchamber 24' and the obturator plenum 11'. FIG. 6 the manifold 20' and the catheter 4' in the normal position, wherein the hydraulic fluid subchamber 24' and the fluid pathway subchamber 26' are contracted, the obturator plenum 11' is expanded to its inflated state, thereby closing the catheter lumen 7' which is in its normal state. FIG. 5 shows the manifold 20' a the catheter 4' in the positions assumed when the needle 90' has been inserted to depress the be diaphragm 36' in the same way as the needle 90 was in order to depress the piston 32 and the diaphragm 36 to obtain the positions of the alternate embodiment which are shown in FIG. 4. In FIG. 5 the hydraulic fluid subchamber 24' and the fluid pathway subchamber 26' are expanded, and the obturator plenum 11' and the expansion subchamber 28' are contracted, such that the catheter lumen 7' is open. As is true for the other embodiments, while it is always necessary to contract collapse the obturator 10', and to thereby open the 7' in order to, withdraw or aspirate fluids from body through the catheter lumen 7' it is preferably possible to infuse fluids through the elastic catheter 4' when the obturator plenum 11' is expanded to inflated state and the lumen 7' is expanded to its state.

Figure 7A:
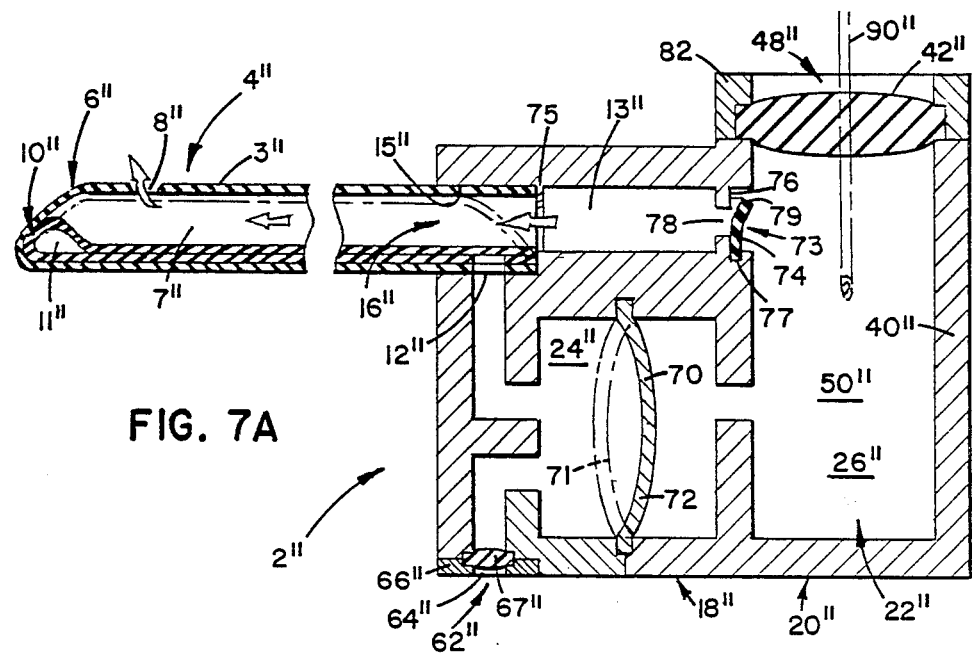
FIG. 7A is an enlarged cross-sectional schematic view taken generally through the center of an intravascular access system having means for hydraulically actuating the catheter obturator including a separation diaphragm having first and second positions.

In FIG. 7A, another embodiment is shown wherein the elements corresponding to e shown in FIGS. 1-6 are designated by double primed reference numerals. The manifold 20" include a separation diaphragm 70 which preferably has two positions 71 and 72 thereby allowing for the relative expansion and contraction of the hydraulic fluid subchamber 24" and the fluid pathway subchamber 26". However, the diaphragm may be either bistable in case the diaphragm 70 is stable in either the or second positions 71 or 72, or monostable in case the diaphragm 70 is stable only in the first position 71. When the separation diaphragm 70 is in first position 71, as is shown in phantom in FIG. 7A, the obturator plenum 11" is expanded to its inflated state such that the obturator 10" substantially blocks the catheter lumen 7", thereby closing the 7" which is in its normal state, so that substantially no fluid can pass through the lumen 7". The embodiment shown in FIG. 7A may be hydraulically actuated inserting a hypodermic needle 90" through the 42" and into the fluid pathway subchamber 26". Fluid may then be abruptly withdrawn or aspirated from the fluid pathway subchamber 26" to manipulate the separation diaphragm 70 by employing fluid pressure such that the diaphragm 70 shifts from the first position 71 to the second position 72 in the distable embodiment. This can be accomplished because the catheter lumen 7" is closed and, therefore, there is no fluid opening to the outside. When the diaphragm 70 occupies the second position 72, the volume within the hydraulic fluid subchamber 24" is increased from the volume of the hydraulic fluid subchamber 24" when the diaphragm 70 occupies the first position 71. This increase in volume is filled by fluid drawn from the obturator plenum 11", thereby contracting the volume of the obturator plenum 11", collapsing the obturator 10 and opening the lumen 7" so that fluid may pass in and out of the catheter opening 8". When the diaphragm 70 is in the second position 72, body fluids, preferably blood, may be withdrawn from the body of the patients in which the manifold 20" is embedded. This may be accomplished by simply aspirating or withdrawing fluid with a hypodermic needle 90" which is inserted in the fluid pathway subchamber 26". Fluids may be infused through the catheter 4" by infusing fluids into the fluid pathway subchamber 26" which pass into the catheter lumen 7" through the catheter access passageway 13", which is a part of the fluid pathway subchamber 26", and into the catheter lumen 7". In the embodiment shown in FIG. 7A, when fluids pass into the catheter access passageway 13" after being infused through the hypodermic needle 90" into the fluid pathway subchamber 26", they must pass around a check valve mechanism 73 which is spring biased to stand open and allow access to the catheter access passageway 13". The fluids may then pass into the catheter the lumen 7" when the lumen 7" is open. The check valve mechanism 73, preferably, includes a resilient rubber check valve flap 74 having first and second ends, 77 and 79. The first end 77 is sealingly engaged to the housing 18". The resilient flap 74 is spring biased so that the second end 79 stands away from the housing 18" and allows fluid to pass through a catheter passageway opening 78.

The catheter 4" is received in the manifold 20" in a catheter receiving passageway 15". The catheter 4" abutts against ridge 75 which conforms to the catheter receiving passageway 15" which receives the proximal end 19" of the catheter 4". In the preferred embodiment, the catheter 4" will be sealed to the housing 18 using a silicone rubber sealant, such as Silastic TM Medical Adhesive Silicone Type A Sealant (Dow Corning, Inc.).

In order to close the catheter lumen 7" when it is in its normal state, the diaphram 70 must be returned from the second position 72 shown in FIG. 7A, to the first position 71 shown in phantom in FIG. 7A. In order to accomplish this shift, in the case of a bistable separation diaphragm 70, fluid are abruptly infused into the fluid pathway subchamber 26" through a hypodermic needle 90" inserted through the access septum 42". This abrupt infusion of fluids will push the second end 79 of the flap 74 against a catheter passageway opening ledge 76, thereby closing the catheter passageway opening 78 and substantially preventing fluids from passing into the catheter access passageway 13". The fluid pressure of the abrupt infusion of fluids is thereby directed primarily to the snap diaphragm 70 which is then shifted from the second stable position 72 to the first stable position 71. Simultaneously, the obturator plenum 11" expanded to its inflated state by fluids simultaneously leaving the hydraulic fluid subchamber 24" and entering the obturator plenum 11" via the obturator opening 12", such that the obturator 10" blocks the catheter lumen 7" as shown in phantom. At the same time, some of the fluids which are in the catheter lumen 7" will backflush toward the check valve flap 74, urging it to open again. The only time the flap 74 is closed, thereby preventing fluid access to the catheter access passageway 13", is when there is a sudden surge of fluid pressure from a hypodermic needle 90" inserted through the access septum 42". When the infusion from the hypodermic needle 90" is less than a sudden surge, the fluid can pass around the flap 74 and into the catheter access passageway 13" without pressing the spring biased flap 74 against the ledge 76.

Figure 7B:
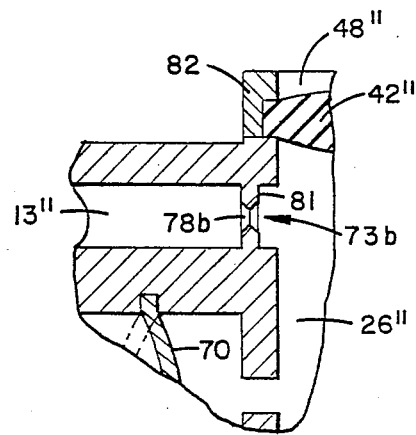
FIG. 7B is an enlarged cross-sectional view of a restricted orifice which is substituted for the check valve mechanism in the embodiment shown in FIG. 7A.

Referring now to FIG. 7B, an alternate embodiment of the embodiment shown in FIG. 7A does not require the check valve mechanism 73. In this embodiment the catheter passageway opening 78b is sufficiently restricted by an orifice restricting mechanism 73b for restricting fluid communication between the fluid pathway subchamber 26" and the catheter lumen 7" catheter passageway opening 78b, preferably including a restrictive orifice collar 81, such that a sudden surge of fluid in or out of the fluid pathway subchamber 26" will be effective to create a transient pressure drop across the passageway opening 78b, which will facilitate the movement of the diaphragm 70 from one position to another.

Another embodiment of the prevent invention, shown in FIG. 8 (wherein elements corresponding to elements in other drawings are triple primed), preferably includes a separation diaphragm 70''', and an orifice restricting mechanism 73B''', preferably including a restrictive orifice collar 81'''. The separation diaphragm 70''' is preferably stable only in the first position 71'''. Fluids can be withdrawn or aspirated from the body by inserting a hypodermic needle 90''' into the fluid pathway subchamber 26''' and withdrawing pressure to move the separation diaphragm 70''' from its first position 71''' toward or to the second position 72" shown in phantom. As the diaphragm 70''' moves away from the first position 71''', the obturator plenum 11''' contracts and the lumen 7''' opens, allowing fluids to be drawn into the manifold 20''', through the catheter lumen 7''' as is the case for the embodiment shown in FIG. 7A. The diaphragm 70''' need not reach the second position 72''', wherein the obturator 10''' would be fully collapsed, in order to allow fluids to be aspirated through the catheter lumen 7'''. When the fluid pressure being exerted to withdrawn fluids ceases, the separation diaphragm 70''' returns to the first position 71''' which is its only stable position. The diaphragm 70''' is preferably spring biased such that it will return to the stable position 71''' when the pressure ceases. In this embodiment, therefore, the obturator 10''' is preferably a variable control mechanism for variably opening the lumen 7''' depending upon how much pressure is exerted upon the separation diaphragm 70'''. The diaphragm 70''' will preferably spring back to the first position 71''' when the force being exerted is sufficiently reduced to allow it to do so. Preferably, a flow restriction mechanism such as the orifice collar 81''' will be employed to restrict the flow of fluids through the catheter passageway opening 78b''' such that a transient pressure drop across the opening 78b''' can be created, thereby facilitating the fluid pressure actuation of the separation diaphragm 70'''. The pressure drop will facilitate the movement of the diaphragm 70''' away from the stable position 71''', and will facilitate the opening of the lumen 7'''.

In this embodiment, fluids are preferably infused into the body through the catheter lumen 7''' when the obturator plenum 11''' is in its inflated state and the lumen 7" is in its expanded state as shown in FIG. 8. Fluids are infused into the body by infusing them into the fluid pathway subchamber 26''', with sufficient pressure to expand the outer tube 6''' of flexible catheter 4''', such that the lumen 7''' is in its expanded state thereby allowing the fluids to pass into the body from the fluid pathway subchamber 26''' via the catheter lumen 7'''. It will be appreciated that if sufficient pressure to expand the catheter 4''' can be exerted upon the outer wall 5''', fluid will be passing through the lumen 7''' and out of the catheter 4''' at a sufficient rate and under a sufficient pressure so as to substantially prevent any diffusion in. When the infusion operation is completed, the catheter lumen 7''' returns to an unexpanded, normal state wherein fluids are no longer able to pass through the lumen 7''' when the obturator plenum 11''' is in its inflated state.

The embodiments of the present invention shown in FIGS. 7A–8 also have a second entry mechanism 64" sealed by a priming septum 67" which allows the amount of fluid in the hydraulic fluid subchamber 24''' to be adjusted. The septum 67" is compressed within the manifold body 40" by a priming septum washer 66" which is welded to the manifold body 40". The space for receiving the septum 67" between the priming septum washer 66" and the manifold body 40" is smaller than the thickness of the septum 67" and, therefore, compresses the outer edge of the resilient self-sealing septum 67" when the seal is effected. A similar relationship exists between the access septum 42" and a first entry washer 82 which presses the access septum 42" against the manifold body 40". The washer 82 is preferably welded to the manifold body 40". Since the space for receiving the septum 42" is once again smaller than the outer edge of the septum 42", the outer edge of the septum 42" is compressed when the seal is effected.

The manifold 20 of the present invention may be constructed of any substantially solid, inert, biocompatible material, such as metal, preferably stainless steel, titanium alloy, or the like; or synthetic, polymeric or plastic materials, such as polysulfone, polycarbonate, and the like. Elements of the manifold may be bonded together by any methods know in the art for joining such materials. Metal parts are preferably joined by welding. Plastic parts may be joined using appropriate compounds known in the art to be useful to join such parts for a similar medical use. The catheter 4 may be the same as the catheter is fully described in co-pending U.S. patent application Ser. No. 367,683 which is incorporated herein by reference. The catheter is made of one of any of a number of flexible, inert, non-toxic, bio-compatible rubber or synthetic rubber-like materials. A preferred material is silicone rubber tubing. In the embodiments shown in FIGS. 3-7, the obturator 10 is preferably at least partially joined to the wall 5 of the catheter 4 at its proximal end 19. Other portions of the obturator 10 engage the wall 5 of the catheter 4 in a non-adherent manner. Preferably, the outer surface 3 and the wall 5 of the catheter 4 are coated with a thin layer of nonadherent material such as fluorine yielding a surface similar to polytetrafluoroethylene (Teflon ™). A thin layer may be applied as, for example, by plasma coating techniques, preferably by glow discharge polymerization. Such a non-adherent coating will substantially prevent the surfaces of silicone rubber tubing from sticking together and bonding. On the other hand, partially coated tubing may be dipped in silicone rubber to form an outer tubing which will adhere to the uncoated areas. In order to bond silicone rubber tubing to plastic surfaces of the housing 18, the plastic surfaces must be prepared using appropriate techniques which will allow a silicone rubber sealant to effectively band the silicone rubber to the plastic surfaces.

The intravascular access system 2 of the present invention is implanted using standard surgical techniques. Proper installation results in the catheter 4 being threaded into the desired blood vessel and the manifold 20 being secured in the subcutaneous tissue with the access septum 46 facing the skin. After implantation, intravascular access is maintained in the dormant state in which the actuating mechanism 22 is maintained in the normal, or dormant position. In this state, the fluid pathway subchamber 26 is preferably filled with a fluid, preferably a saline solution or an antiseptic solution, in order to prevent bacterial growth and any possible infection. The catheter lumen 7 in the space between the wall 5 and the obturator 10 is closed with the exception of a small area at the proximal end 19 of the catheter 4. It will be appreciated that when the catheter 4 is substantially blocked such that no fluid can diffuse through the lumen 7, the lumen 7 is closed. This occurs when the obturator plenum 11 is fully expanded and the obturator 10 blocks the catheter lumen 7. When the lumen 7 is closed, however, fluids can be infused through the closed lumen 7 into the body when the fluids are infused into the manifold 20 with sufficient pressure to expand the elastic outer tube 6 of the catheter 4.

The puncturable, self-sealing resilient septums used in the embodiments of the present invention are made of silicone rubber. Preferably, these septums are designed so that they will be especially selfsealing, wherein the silicone rubber will reknit so that no opening will remain where a needle was once inserted. Septums with this characteristic are well known in the art.

The fluid in the hydraulic fluid subchamber 24 and the obturator plenum 11 is preferably a hyperosmotic fluid, such as glycerol or an aqueous solution of sodium chloride, sucrose or the like. When the obturator plenum 11 and the hydraulic fluid subchamber 24 are filled with hydraulic fluid during the assembly of the intravascular access system 2 it is possible that a small amount of gas, most likely air, will be allowed into the obturator plenum 11. This could cause a system failure if expansion of the hydraulic fluid subchamber 24 is accompanied by significant expansion or trapped gas bubbles. In that case, sufficient fluid may not be withdrawn from the obturator plenum 11 in order to open the catheter lumen 7.

In order to avoid this potential problem, it is important to use a hydraulic fluid which is hyperosmotic with respect to body fluids. Silicone rubber, which is preferably used to make the obturator 10, is very slightly permeable to fluids, such as water, and to gases such as $O_2$ and $CO_2$. If aqueous fluids of different osmolarity are separated by a permeable membrane, osmotic pressure will urge water to permeable through the membrane until osmotic equilibrium is achieved. Therefore, the hyperosmotic fluid in the obturator plenum 11 will tend to draw water from body fluids into the obturator plenum 11 across the silicone rubber obturator 10 which separates the obturator plenum 11 from the catheter lumen 7. This increases the hydrostatic pressure in the obturator plenum 11, which in turn will tend to drive gases, which permeate more easily through silicone rubber than the water, out of the obturator plenum 11 and into the body fluids. Ultimately, air bubbles will be purged from the system and the elastic forces of the silicone rubber catheter 4, hydrostatic pressure and osmotic pressure will come into equilibrium.

Because the implantable catheter obturator controller manifold of the present invention is designed to be implanted under the skin of a patient, it is desirable to limit the size of the manifold. Preferably, the manifold has a cylindrical body which is about 2-4 inches in diameter (approximately 5.0-10.0 cm) and about 0.5-2 inches thick (approximately 1.25-5.0 cm). It will be appreciated that the manifold need not have a cylindrical shape, but that thin shape is preferable for reasons of both ease of manufacturing and ease of use.

While certain representative embodiments of the present invention have been described herein for the purposes of illustration, it will be apparent to those skilled in the art that modifications therein may be made without departing from the spirit and scope of the present invention.

What is claimed is:

1. An implantable, catheter obturator controller manifold for use with an implantable intravascular catheter including a lumen having a normal state and an expanded state, an obturator, and an obturator plenum having an inflated state and a contracted state, wherein the lumen can be closed or opened when it is in its normal state by hydraulically actuating the expansion or contraction of the obturator plenum, wherein when the obturator plenum is expanded to its inflated state, the lumen is substantially blocked by the obturator when the lumen is in its normal state such that substantially no fluid can pass through the lumen, the manifold comprising:
   (a) a housing;
   (b) first entry means for entering the housing;
   (c) receiving means for receiving the catheter in the housing; and
   (d) actuating means for hydraulically actuating the contraction or expansion of the obturator plenum, said actuating means including:
   (i) a manifold chamber within the housing in fluid communication with the catheter, said manifold chamber including at least two subchambers separated from each other, a fluid pathway subchamber adapted for fluid communication with the lumen of the catheter and the first entry means, and a hydraulic fluid subchamber in fluid communication with the obturator plenum; said fluid pathway subchamber and said hydraulic fluid subchamber being expandable and contractible; and (ii) an amount of a hydraulic fluid effective to actuate the expansion and contraction of the obturator plenum, said fluid being adapted to be contained within the hydraulic fluid subchamber and the obturator plenum, and said amount of fluid being sufficient to allow the obturator to effectively block the lumen when the lumen is in its normal state and the obturator is expanded to its inflated state.

2. The implantable, catheter obturator controller manifold of claim 1 wherein said first entry means include a puncturable, self-sealing, resilient access septum which seals said first entry means.

3. The implantable, catheter obturator controller manifold of claim 2 including adjusting means for adjusting the amount of hydraulic fluid within the hydraulic fluid subchamber and the obturator plenum.

4. The implantable, catheter obturator controller manifold of claim 3 wherein said adjusting means include second entry means for entering said housing; said second entry means being in fluid communication with said hydraulic fluid subchamber; said second entry means including a puncturable, self-sealing, resilient priming septum which seals said second entry means; wherein the amount of hydraulic fluid in said hydraulic fluid subchamber may be adjusted by infusing fluid into, or withdrawing fluid from, said hydraulic fluid subchamber using a hypodermic needle inserted through said priming septum.

5. The implantable, catheter obturator controller manifold of claim 2 wherein said actuating means include a separation diaphragm between the hydraulic fluid subchamber and the fluid pathway subchamber having first and second stable positions; said fluid pathway subchamber being adapted to communicate with the catheter lumen via a catheter passageway opening; wherein the separation diaphragm cooperates with the hydraulic fluid in the hydraulic fluid subchamber and the obturator plenum to expand the obturator plenum to its inflated state such that the obturator substantially blocks the catheter lumen when the diaphragm is in the first stable position and the lumen is in its normal state, and to contract the obturator plenum such that the catheter lumen is open when the diaphragm is in the second stable position.

6. The implantable, catheter obturator controller manifold of claim 5 wherein said actuating means include check valve means for blocking fluid communication between the fluid pathway subchamber and the catheter lumen via the catheter passageway opening such that a surge of fluid pressure into said fluid pathway subchamber closes said check valve means such that fluid cannot pass into the catheter lumen from the fluid pathway subchamber, wherein the surge of fluid pressure effectively manipulates the separation diaphragm from the second stable position to the first stable position, thereby expanding the obturator plenum to its inflated state and substantially blocking the catheter lumen when the lumen is in its normal state.

7. The implantable, catheter obturator controller manifold of claim 5 wherein said actuating means include orifice restricting means for restricting fluid communication between the fluid pathway subchamber and the catheter lumen via the catheter passageway opening such that a surge of fluid pressure into said fluid pathway subchamber effectively manipulates the separation diaphragm from the second stable position to the first stable position, thereby expanding the obturator plenum to its inflated state such that the obturator substantially blocks the catheter lumen when the lumen is in its normal state.

8. The implantable, catheter obturator controller manifold of claim 2 wherein said actuating means include first expansion means for expanding and contracting said hydraulic fluid subchamber such that the hydraulic fluid subchamber can be expanded so that said fluid is at least partially withdrawn from the obturator plenum, thereby contracting the obturator plenum and opening the catheter lumen, and such that, subsequently, the hydraulic fluid subchamber can be contracted such that said fluid expands the obturator plenum to its inflated state, the obturator substantially blocks the catheter lumen when the lumen is in its normal state, and substantially no fluid can diffuse through the lumen.

9. The implantable, catheter obturator controller manifold of claim 8 wherein said actuating means include an expansion subchamber; said expansion subchamber having an expandable and contractable volume; said volume being at least partially occupied by a compressible gas; wherein said expansion subchamber cooperates with said hydraulic fluid subchamber to allow the expansion of the hydraulic fluid subchamber into space occupied by said expansion subchamber.

10. The implantable, catheter obturator controller manifold of claim 9 wherein said actuating means include second expansion means for expanding and contracting said fluid pathway subchamber; wherein said second expansion means cooperates with said first expansion means and said expansion subchamber, such that the expansion or contraction of the volume of said expansion subchamber is substantially equivalent to the contraction or expansion of the fluid pathway subchamber and the hydraulic fluid subchamber taken together 11. The implantable, catheter obturator controller manifold of claim 10 wherein said actuating means include a first bellows mechanism including a first bellows and a rigid bellows diaphragm, wherein the first bellows is attached to the bellows diaphragm and the housing such that the first bellows and the diaphragm separate the hydraulic fluid subchamber from the expansion subchamber.

12. The implantable, catheter obturator controller manifold of claim 11 wherein said acuating means include a second bellows mechanism including a second bellows, wherein the second bellows is attached to the bellows diaphragm and the housing such that the second bellows separates said fluid pathway subchamber from said hydraulic fluid subchamber.

13. The implantable, catheter obturator controller manifold of claim 11 wherein said actuating means include telescoping means for separating said fluid pathway subchamber from said hydraulic fluid subchamber, said telescoping means including a cylindrical piston inside of a sleeve of slightly larger diameter; said piston equipped with at least one resilient O-ring located on the cylindrical surface of the piston such that the piston, the O-ring, and the sleeve cooperate to form an expandable telescoping joint which is sealed to said bellows diaphragm and to said housing to substantially prevent fluid communication between the fluid pathway subchamber and the hydraulic fluid subchamber.

14. The implantable, catheter obturator controller manifold of claim 2 wherein said actuating means include a separation diaphragm between the hydraulic fluid subchamber and the fluid pathway subchamber having a single stable position; said fluid pathway subchamber communicating with the catheter lumen via a catheter passageway opening; wherein the separation diaphragm cooperates with the hydraulic fluid in the hydraulic fluid subchamber and the obturator plenum to expand the obturator plenum to its inflated state such that the obturator substantially blocks the catheter lumen when the diaphragm is in the stable position and the lumen is in its normal state; and wherein a surge of fluid pressure away from said separation diaphragm can move said diaphragm away from the stable position thereby expanding the hydraulic fluid subchamber and contracting the obturator plenum such that the catheter lumen is open for fluids to pass through.

15. The implantable catheter obturator controller manifold of claim 14 wherein said actuating means include orifice restricting means for restricting fluid communication between the fluid pathway subchamber and the catheter lumen via the catheter passageway opening such that a surge of fluid pressure withdrawn from said fluid pathway subchamber is effective to create a transient pressure drop across said restricting means and such that the pressure drop facilitates the opening of the catheter lumen; and wherein the catheter lumen is adapted to be expanded to its expanded state when the obturator plenum is in its inflated state by infusing fluids into the fluid pathway subchamber under sufficient pressure to expand the catheter thereby allowing fluids to pass through the lumen when the obturator plenum is in its inflated state.

16. An implantable intravascular access system comprising:
  (a) a flexible intravascular catheter including a lumen having a normal state and an expanded state, an obturator, and an obturator plenum having an inflated state and a contracted state, wherein the lumen can be closed or opened by hydraulically actuating the expansion or contraction of the obturator lumen, wherein the lumen is substantially blocked by the obturator such that substantially no fluid can pass through the lumen when the obturator plenum is expanded to its inflated state and the lumen is in its normal state;
  (b) a housing;
  (c) first entry means for entering the housing;
  (d) receiving means for receiving the catheter in the housing; and
  (e) actuating means for hydraulically actuating the contraction or expansion of the obturator plenum, said actuating means including:
    (i) a manifold chamber within the housing in fluid communication with the catheter, said manifold chamber including at least two subchambers separated from each other, a fluid pathway subchamber in fluid communication with the lumen of the catheter and the first entry means, and a hydraulic fluid subchamber in fluid communication with the obturator plenum; said fluid pathway subchamber and said hydraulic fluid subchamber being expandable and contractable; and
    (ii) an amount of a hydraulic fluid effective to actuate the expansion and contraction of the obturator plenum, said fluid being contained in the hydraulic fluid subchamber and the obturator plenum, and said amount of fluid being sufficient to allow the obturator to effectively block the lumen when the lumen is in its normal state and the obturator plenum is expanded to its inflated state.

17. The implantable intravascular access system of claim 16 including adjusting means for adjusting the amount of hydraulic fluid within the hydraulic fluid subchamber and the obturator plenum; said adjusting means including second entry means for entering the housing which communciate with said hydraulic fluid subchamber; said first entry means including a puncturable, self-sealing, resilient access septum which seals said first entry means; and said second entry means including a puncturable, self-sealing, resilient priming septum which seals said second entry means; said fluid pathway subchamber communicating with the catheter lumen via a catheter passagway opening; wherein said amount of hydraulic fluid in said hydraulic fluid subchamber and said obturator plenum may be adjusted by infusing fluid into, or withdrawing fluid from, said hydraulic fluid subchamber using a hypodermic needle inserted through said priming septum.

18. The implantable intravascular access system of claim 17 wherein said actuating means include a separation diaphragm having first and second stable positions and orifice restricting means for restricting fluid communication between the fluid pathway subchamber and the catheter lumen via the catheter passageway opening; wherein the separation diaphragm cooperates with the hydraulic fluid in the hydraulic fluid subchamber and the obturator plenum to expand and contract the obturator plenum such that the obturator substantially blocks the catheter lumen when the lumen is in its normal state and the separation diaphragm is in the first stable position, and such that the obturator plenum contracts such that the catheter lumen is open when the separation diaphragm is in the second stable position; and wherein said orifice restricting means can restrict communication between the fluid pathway subchamber and the catheter lumen via the catheter passageway opening, such that a surge of fluid pressure into said fluid pathway subchamber effectively manipulates the separation diaphragm from the second stable position to the first stable position, thereby fully expanding the obturator plenum to its inflated state and substantially blocking the catheter lumen when the lumen is in its normal state.

19. The implantable, intravascular access system of claim 18 wherein said actuating means include a first bellows mechanism including a first bellows and a rigid bellows diaphragm; said first bellows being attached to the bellows diaphragm and the housing such that the first bellows and the diaphragm separate the hydraulic fluid subchamber from the expansion subchamber.

20. The implantable, intravascular access system of claim 19 wherein said actuating means include a second bellows mechanism including a second bellows; said second bellows being attached to the bellows diaphragm and the housing such that the second bellows separates said fluid pathway subchamber from said hydraulic fluid subchamber.

21. The implantable, intravascular access system of claim 19 wherein said actuating means include telescoping means for separating said fluid pathway subchamber from said hydraulic fluid subchamber, said telescoping means including a cylindrical piston inside of a sleeve of slightly larger diameter, said piston equipped with at least one resilient O-ring located on the cylindrical surface of the piston such that the piston, the O-ring, and the sleeve cooperate to form an expandable telescoping joint which is sealed to said bellows diaphragm and to said housing to substantially prevent fluid communication between the fluid pathway subchamber and the hydraulic fluid subchamber.

22. The implantable intravascular access system of claim 18 wherein said catheter lumen can be expanded to the expanded state when the obturator plenum is in its inflated state and fluid is infused into the fluid pathway subchamber with sufficient fluid pressure to expand the catheter, thereby allowing fluid to pass through the lumen when the obturator plenum is in its inflated state.

23. The implantable intravascular access system of claim 17 wherein said actuating means include an expansion subchamber; first expansion means for expanding and contracting said hydraulic fluid subchamber; and second expansion means for expanding and contracting said fluid pathway subchamber; said expansion subchamber containing an expandable and contractible volume; said volume being at least partially occupied by a compressible gas; wherein said second expansion means cooperate with said first expansion means and said expansion subchamber, such that the expansion or contraction of the volume of said expansion subchamber substantially relates to the contraction or expansion of the fluid pathway subchamber and the hydraulic fluid subchamber together; and wherein the hydraulic fluid subchamber may be expanded such that fluid is withdrawn from the obturator plenum, thereby contracting the obturator plenum and opening the catheter lumen, and such that the hydraulic fluid subchamber may be subsequently contracted such that the fluid expands the plenum to its inflated state, causing the obturator to substantially block the lumen when the lumen is in its normal state such that substantially no fluid can pass through the lumen.

24. The implantable intravascular access system of claim 16 wherein said actuating means include a separation diaphragm between the hydraulic fluid subchamber and the fluid pathway subchamber having a single stable position; said fluid pathway subchamber communicating with the catheter lumen via a catheter passageway opening; wherein the separation diaphragm cooperates with the hydraulic fluid in the hydraulic fluid subchamber and the obturator plenum to expand the obturator plenum to its inflated state such that the obturator substantially blocks the catheter lumen when the diaphragm is in the stable position and the lumen is in its normal state; and wherein a surge of fluid pressure away from said separation diaphragm can move said diaphragm away from the stable position thereby expanding the hydraulic fluid subchamber and contracting the obturator plenum such that the catheter lumen is open for fluid to pass through.

25. The implantable catheter obturator controller manifold of claim 24 wherein said actuating means include orifice restricting means for restricting fluid communication between the fluid pathway subchamber and the catheter lumen via the catheter passageway opening such that a surge of fluid pressure withdrawn from said fluid pathway subchamber is effective to create a transient pressure drop across said restricting means and such that the pressure drop facilitates the opening of the catheter lumen; and wherein the catheter lumen can be expanded to its expanded state when the obturator plenum is in its inflated state by infusing fluids into the fluid pathway subchamber under sufficient pressure to expand the catheter, thereby allowing fluids to pass through the lumen when the obturator plenum is in its inflated state.

26. The implantable intravascular access system of claim 16 wherein said actuating means include a separation diaphragm having first and second stable positions and check valve means for blocking fluid communication between the fluid pathway subchamber and the catheter lumen via the catheter passageway opening; wherein the separation diaphragm cooperates with the hydraulic fluid in the hydraulic fluid subchamber and the obturator plenum to expand and contract the obturator plenum such that the obturator substantially blocks the catheter lumen when the separation diaphragm is in the first stable position and the lumen is in its normal state and such that the obturator plenum contracts such that the catheter lumen is open when the separation diaphragm is in the second stable position; and wherein said check valve means can block communication between the fluid pathway subchamber and the lumen of the catheter via the catheter passageway opening, such that a surge of fluid pressure into said fluid pathway subchamber closes said check value means such that fluid cannot pass into the catheter lumen from the fluid pathway subchamber, and wherein the urge of fluid pressure can more effectively manipulate the separation diaphragm from the second stable position to the first stable position, thereby expanding the obturator plenum to its inflated state and substantially blocking the catheter lumen when the lumen is in its normal state.

* * * * *

UNITED STATES PATENT AND TRADEMARK OFFICE
CERTIFICATE OF CORRECTION

PATENT NO. : 4,846,806
DATED : July 11, 1989
INVENTOR(S) : Wigness et al.

It is certified that error appears in the above-identified patent and that said Letters Patent is hereby corrected as shown below:

On the Title page, under "Assignee", "501 Regents of University of Minnesota" should read --Regents of the University of Minnesota--.

In Col. 1, line 58, insert --,-- after the word "however".

In Col. 2, line 33, "tissure" should read --tissue--.

In Col. 2, line 42, insert --1-- after the word "often".

In Col. 3, lines 21 and 22, insert --;-- after the word "housing".

In Col. 3, line 29, "or" should read --of--.

In Col. 3, line 57, insert --subchamber using a hypodermic needle inserted through-- after the word "fluid".

In Col. 4, line 13, "1" should read --lumen--.

In Col. 4, line 14, "how" should read --however,--.

In Col. 4, line 15, insert --access-- after the word "requires".

In Col. 4, line 16, insert --lumen-- after the word "catheter".

In Col. 4, line 17, insert --possible-- after the word "is".

In Col. 4, line 18, "S" should read --single--.

In Col. 4, line 18, insert --allows-- after the word "This".

In Col. 4, line 19, insert --chamber-- after the word "the".

UNITED STATES PATENT AND TRADEMARK OFFICE
CERTIFICATE OF CORRECTION

PATENT NO. : 4,846,806
DATED : July 11, 1989
INVENTOR(S) : Wigness et al.

It is certified that error appears in the above-identified patent and that said Letters Patent is hereby corrected as shown below:

In Col. 4, line 20, "shift" should read --shifting--.

In Col. 4, line 37, "make" should read --makes--.

In Col. 5, line 1, "s" should read --is--.

In Col. 7, line 17, insert --.-- after the word "normal".

In Col. 7, line 21, insert --,-- after the numeral "10".

In Col. 7, line 35, "obturato" should read --obturator--.

In Col. 7, line 41, insert --.-- after the word "state".

In Col. 7, line 45, insert --catheter-- after the word "the".

In Col. 7, line 47, insert --to-- after the word "designed".

In Col. 7, line 52, insert --problems-- after the word "the".

In Col. 7, line 53, insert --catheter-- after the word "the".

In Col. 7, line 54, insert --actuate-- after the word "to".

In Col. 7, line 55, insert --have been-- after the word "invention".

In Col. 7, line 56, insert --receiving-- after the letter "a".

In Col. 7, line 57, "pas" should read --passageway--.

In Col. 7, line 58, insert --catheter-- after the word "the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 7, line 61, insert --of-- after the word "expansion".

In Col. 7, line 62, insert --includes-- after the numeral "22".

In Col. 7, line 65, "s" should read --subchamber--.

In Col. 7, line 66, insert --plenum-- after the word "obturator".

In Col. 7, line 67, "s" should read --subchamber--.

In Col. 7, line 67, insert --of the-- after the numeral "7".

In Col. 8, line 1, insert --fluid-- after the word "hydraulic".

In Col. 8, line 3, insert --the-- after the word "actuate".

In Col. 8, line 4, insert --11-- after the word "plenum".

In Col. 8, line 9, "attach" should read --attached--.

In Col. 8, line 10, "e" should read --elements--.

In Col. 8, line 11, insert --subchamber-- after the word "pathway".

In Col. 8, line 13, insert --subchamber-- after the word "pathway".

In Col. 8, line 14, insert --, the bellows-- after the word "Preferably".

In Col. 8, line 14, insert --are-- after the numeral "29".

In Col. 8, line 16, "des" should read --designed--.

UNITED STATES PATENT AND TRADEMARK OFFICE
CERTIFICATE OF CORRECTION

PATENT NO. : 4,846,806

DATED : July 11, 1989

INVENTOR(S) : Wigness et al.

Page 4 of 8

It is certified that error appears in the above-identified patent and that said Letters Patent is hereby corrected as shown below:

In Col. 8, line 18, insert --sleeve-- after the word "collared".

In Col. 8, line 19, "e" should read -- engaged--.

In Col. 8, line 20, insert --a-- after the word "providing".

In Col. 8, line 22, "th" should read --the--.

In Col. 8, line 22, insert --hydraulic-- after the word "the".

In Col. 8, line 28, insert --when-- after the word "embodiment,".

In Col. 8, line 40, insert --is-- after the word "it".

In Col. 8, line 53, "bee" should read --been--.

In Col. 8, line 58, insert --through-- after the word "flow".

In Col. 8, line 60, insert --of-- after the word "out".

In Col. 9, line 1, insert --catheter-- after the word "the".

In Col. 9, line 7, "cath" should read --catheter--.

In Col. 9, line 11, insert --,-- after the word "embodiment".

In Col. 9, line 51, "tube outer 6" should read --outer tube 6--.

In Col. 9, line 60, insert --thereby-- after the word "state".

In Col. 9, line 63, insert --in-- after the word "shown".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 10, line 63, insert --the-- after the word "between".

In Col. 11, line 1, delete "of and" after the word "joints".

In Col. 11, line 7, "mean" should read --means--.

In Col. 11, line 22, "differences" should read --difference--.

In Col. 11, line 27, "be" should read --bellows--.

In Col. 11, line 31, insert --passageway-- after the word "priming".

In Col. 11, line 32, insert --.-- after the numeral "63".

In Col. 11, line 33, insert --between-- after the word "communication".

In Col. 11, line 34, insert --portion-- after the word "main".

In Col. 11, line 35, insert --catheter-- after the word "The".

In Col. 11, line 35, insert --obturator opening-- after the word "the".

In Col. 11, line 37, insert --shows-- after the numberal "6".

In Col. 11, line 38, insert --dormant-- after the word "normal,".

In Col. 11, line 40, insert --and-- after the word "contracted,".

In Col. 11, line 43, "a" should read --and--.

In Col. 11, line 44, insert --hypodermic-- after the word "the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 11, line 45, "be" should read --bellows--.

In Col. 11, line 46, insert --inserted-- after the word "was".

In Col. 11, line 54, insert --lumen-- after the word "the".

In Col. 11, line 55, insert --the-- after the word "from".

In Col. 11, line 58, insert --its-- after the word "to".

In Col. 11, line 59, insert --expanded-- after the word "its".

In Col. 11, line 61, "e" should read --elements--.

In Col. 11, line 63, "include" should read --includes--.

In Col. 11, line 64, insert --stable-- after the word "two".

In Col. 11, line 68, insert --which-- after the word "in".

In Col. 12, line 1, insert --first-- after the word "the".

In Col. 12, line 1, insert --which-- after the word "in".

In Col. 12, line 3, insert --the-- after the word "in".

In Col. 12, line 7, insert --lumen-- after the word "the".

In Col. 12, line 10, insert --by-- after the word "actuated".

In Col. 12, line 11, insert --access septum-- after the words "through the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 12, line 30, "patients" should read --patient--.

In Col. 12, line 56, insert --a catheter-- after the word "against".

In Col. 12, line 64, "diaphram" should read --diaphragm--.

In Col. 12, line 68, "fluid" should read --fluids--.

In Col. 13, line 11, insert --is-- after the word "plenum 11".

In Col. 13, line 34, insert --via the-- after the word "lumen 7".

In Col. 13, line 46, delete "," after the numeral "73B'''".

In Col. 13, line 51, insert --fluid from the subchamber 26''' with sufficient fluid-- after the word "withdrawing".

In Col. 13, line 57, delete "," after the numeral "20'''".

In Col. 13, line 63, "withdrawn" should read --withdraw--.

In Col. 14, line 18, "lumen 7'''" should read --lumen 7'''--.

In Col. 14, line 39, "24'''" should read --24''--.

In Col. 14, lines 56 and 57, "biocompatible" should read --bio-compatible--.

In Col. 14, line 66, insert --which-- after the word "catheter".

In Col. 15, line 23, "band" should read --bond--.

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 15, line 50, insert --,-- after the word "self-sealing".

In Col. 15, line 53, "selfsealing" should read --self-sealing--.

In Col. 16, line 10, "permeable" should read --permeate--.

In Col. 16, line 32, "thin" should read --this--.

In Col. 18, line 40, in claim 10, insert --.-- after the word "together".

In Col. 19, line 43, in claim 43, "lumen" should read --plenum--.

In Col. 22, line 45, in claim 26, "urge" should read --surge--.

Signed and Sealed this

Tenth Day of November, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,846,806

DATED : July 11, 1989

INVENTOR(S) : Wigness et al.

Page 1 of 8

It is certified that error appears in the above-identified patent and that said Letters Patent is hereby corrected as shown below:

On the Title Page, under "Assignee", "501 Regents of University of Minnesota" should read --Regents of the University of Minnesota--.

In Col. 1, line 58, insert --,-- after the word "however".

In Col. 2, line 33, "tissure" should read --tissue--.

In Col. 2, line 42, insert --a-- after the word "often".

In Col. 3, lines 21 and 22, insert --;-- after the word "housing".

In Col. 3, line 29, "or" should read --of--.

In Col. 3, line 57, insert --subchamber using a hypodermic needle inserted through-- after the word "fluid".

In Col. 4, line 13, "1" should read --lumen--.

In Col. 4, line 14, "how" should read --however,--.

In Col. 4, line 15, insert --access-- after the word "requires".

In Col. 4, line 16, insert --lumen-- after the word "catheter".

In Col. 4, line 17, insert --possible-- after the word "is".

In Col. 4, line 18, "S" should read --single--.

In Col. 4, line 18, insert --allows-- after the word "This".

In Col. 4, line 19, insert --chamber-- after the word "the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 4, line 20, "shift" should read --shifting--.

In Col. 4, line 37, "make" should read --makes--.

In Col. 5, line 1, "s" should read --is--.

In Col. 7, line 17, insert --.-- after the word "normal".

In Col. 7, line 21, insert --,-- after the numeral "10".

In Col. 7, line 35, "obturato" should read --obturator--.

In Col. 7, line 41, insert --.-- after the word "state".

In Col. 7, line 45, insert --catheter-- after the word "the".

In Col. 7, line 47, insert --to-- after the word "designed".

In Col. 7, line 52, insert --problems-- after the word "the".

In Col. 7, line 53, insert --catheter-- after the word "the".

In Col. 7, line 54, insert --actuate-- after the word "to".

In Col. 7, line 55, insert --have been-- after the word "invention".

In Col. 7, line 56, insert --receiving-- after the letter "a".

In Col. 7, line 57, "pas" should read --passageway--.

In Col. 7, line 58, insert --catheter-- after the word "the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 7, line 61, insert --of-- after the word "expansion".

In Col. 7, line 62, insert --includes-- after the numeral "22".

In Col. 7, line 65, "s" should read --subchamber--.

In Col. 7, line 66, insert --plenum-- after the word "obturator".

In Col. 7, line 67, "s" should read --subchamber--.

In Col. 7, line 67, insert --of the-- after the numeral "7".

In Col. 8, line 1, insert --fluid-- after the word "hydraulic".

In Col. 8, line 3, insert --the-- after the word "actuate".

In Col. 8, line 4, insert --11-- after the word "plenum".

In Col. 8, line 9, "attach" should read --attached--.

In Col. 8, line 10, "e" should read --elements--.

In Col. 8, line 11, insert --subchamber-- after the word "pathway".

In Col. 8, line 13, insert --subchamber-- after the word "pathway".

In Col. 8, line 14, insert --, the bellows-- after the word "Preferably".

In Col. 8, line 14, insert --are-- after the numeral "29".

In Col. 8, line 16, "des" should read --designed--.

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 8, line 18, insert --sleeve-- after the word "collared".

In Col. 8, line 19, "e" should read -- engaged--.

In Col. 8, line 20, insert --a-- after the word "providing".

In Col. 8, line 22, "th" should read --the--.

In Col. 8, line 22, insert --hydraulic-- after the word "the".

In Col. 8, line 28, insert --when-- after the word "embodiment,".

In Col. 8, line 40, insert --is-- after the word "it".

In Col. 8, line 53, "bee" should read --been--.

In Col. 8, line 58, insert --through-- after the word "flow".

In Col. 8, line 60, insert --of-- after the word "out".

In Col. 9, line 1, insert --catheter-- after the word "the".

In Col. 9, line 7, "cath" should read --catheter--.

In Col. 9, line 11, insert --,-- after the word "embodiment".

In Col. 9, line 51, "tube outer 6" should read --outer tube 6--.

In Col. 9, line 60, insert --thereby-- after the word "state".

In Col. 9, line 63, insert --in-- after the word "shown".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 10, line 63, insert --the-- after the word "between".

In Col. 11, line 1, delete "of and" after the word "joints".

In Col. 11, line 7, "mean" should read --means--.

In Col. 11, line 22, "differences" should read --difference--.

In Col. 11, line 27, "be" should read --bellows--.

In Col. 11, line 31, insert --passageway-- after the word "priming".

In Col. 11, line 32, insert --.-- after the numeral "63".

In Col. 11, line 33, insert --between-- after the word "communication".

In Col. 11, line 34, insert --portion-- after the word "main".

In Col. 11, line 35, insert --catheter-- after the word "The".

In Col. 11, line 35, insert --obturator opening-- after the word "the".

In Col. 11, line 37, insert --shows-- after the numberal "6".

In Col. 11, line 38, insert --dormant-- after the word "normal,".

In Col. 11, line 40, insert --and-- after the word "contracted,".

In Col. 11, line 43, "a" should read --and--.

In Col. 11, line 44, insert --hypodermic-- after the word "the".

UNITED STATES PATENT AND TRADEMARK OFFICE
CERTIFICATE OF CORRECTION

PATENT NO.   :   4,846,806
DATED        :   July 11, 1989
INVENTOR(S)  :   Wigness et al.

It is certified that error appears in the above-identified patent and that said Letters Patent is hereby corrected as shown below:

In Col. 11, line 45, "be" should read --bellows--.

In Col. 11, line 46, insert --inserted-- after the word "was".

In Col. 11, line 54, insert --lumen-- after the word "the".

In Col. 11, line 55, insert --the-- after the word "from".

In Col. 11, line 58, insert --its-- after the word "to".

In Col. 11, line 59, insert --expanded-- after the word "its".

In Col. 11, line 61, "e" should read --elements--.

In Col. 11, line 63, "include" should read --includes--.

In Col. 11, line 64, insert --stable-- after the word "two".

In Col. 11, line 68, insert --which-- after the word "in".

In Col. 12, line 1, insert --first-- after the word "the".

In Col. 12, line 1, insert --which-- after the word "in".

In Col. 12, line 3, insert --the-- after the word "in".

In Col. 12, line 7, insert --lumen-- after the word "the".

In Col. 12, line 10, insert --by-- after the word "actuated".

In Col. 12, line 11, insert --access septum-- after the words "through the".

UNITED STATES PATENT AND TRADEMARK OFFICE
CERTIFICATE OF CORRECTION

PATENT NO. : 4,846,806

DATED : July 11, 1989

INVENTOR(S) : Wigness et al.

It is certified that error appears in the above-identified patent and that said Letters Patent is hereby corrected as shown below:

In Col. 12, line 30, "patients" should read --patient--.

In Col. 12, line 56, insert --a catheter-- after the word "against".

In Col. 12, line 64, "diaphram" should read --diaphragm--.

In Col. 12, line 68, "fluid" should read --fluids--.

In Col. 13, line 11, insert --is-- after the word "plenum 11".

In Col. 13, line 34, insert --via the-- after the word "lumen 7".

In Col. 13, line 46, delete "," after the numeral "73B'''".

In Col. 13, line 51, insert --fluid from the subchamber 26''' with sufficient fluid-- after the word "withdrawing".

In Col. 13, line 57, delete "," after the numeral "20'''".

In Col. 13, line 63, "withdrawn" should read --withdraw--.

In Col. 14, line 18, "lumen 7'" should read --lumen 7'''--.

In Col. 14, line 39, "24'''" should read --24''--.

In Col. 14, lines 56 and 57, "biocompatible" should read --bio-compatible--.

In Col. 14, line 66, insert --which-- after the word "catheter".

In Col. 15, line 23, "band" should read --bond--.

UNITED STATES PATENT AND TRADEMARK OFFICE
CERTIFICATE OF CORRECTION

PATENT NO. : 4,846,806
DATED : July 11, 1989
INVENTOR(S) : Wigness et al.

It is certified that error appears in the above-identified patent and that said Letters Patent is hereby corrected as shown below:

In Col. 15, line 50, insert --,-- after the word "self-sealing".

In Col. 15, line 53, "selfsealing" should read --self-sealing--.

In Col. 16, line 10, "permeable" should read --permeate--.

In Col. 16, line 32, "thin" should read --this--.

In Col. 18, line 40, in claim 10, insert --.-- after the word "together".

In Col. 19, line 43, in claim 16, "lumen" should read --plenum--.

In Col. 22, line 45, in claim 26, "urge" should read --surge--.

This certificate supersedes Certificate of Correction issued November 10, 1992.

Signed and Sealed this

Ninth Day of August, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   :   4,846,806

DATED         :   July 11, 1989

INVENTOR(S) :   Bruce D. Wigness et al

It is certified that error appears in the above-identified patent and that said Letters Patent is hereby corrected as shown below:

In column 1, line 5, before "FIELD OF THE INVENTION", insert the following paragraph:

--This invention was made with government support under POSCH grant 5R01-HL 15265 awarded by the National Institutes of Health. The government has certain rights in the invention.--

Signed and Sealed this

Thirty-first Day of December, 1996

*Attest:*

BRUCE LEHMAN

*Attesting Officer*     Commissioner of Patents and Trademarks